United States Patent [19]

Hoffmann et al.

[11] 4,075,330
[45] Feb. 21, 1978

[54] O,S-DIALKYL-O-[1-ALKYL-3,4-TRIMETHYLENE-PYRAZOL(5)YL]-THIONOTHIOLPHOSPHORIC ACID ESTER

[75] Inventors: Hellmut Hoffmann, Wuppertal; Ingeborg Hammann, Cologne, both of Germany

[73] Assignee: Bayer Aktiengesellschaft, Leverkusen, Germany

[21] Appl. No.: 767,585

[22] Filed: Feb. 10, 1977

[30] Foreign Application Priority Data

Feb. 26, 1976 Germany .............................. 2607658

[51] Int. Cl.² .......................... C07F 9/65; A01N 9/36
[52] U.S. Cl. ..................................... 424/200; 548/369
[58] Field of Search ......................... 548/369; 424/200

[56] References Cited

U.S. PATENT DOCUMENTS 3,786,065  1/1974  Hoffmann ............................ 548/369

OTHER PUBLICATIONS

Hoffmann Chem. Abst. vol. 74, 1971, 142065b.

Primary Examiner—Natalie Trousof
Assistant Examiner—Jane T. Fan
Attorney, Agent, or Firm—Burgess, Dinklage & Sprung

[57] ABSTRACT

O,S-Dialkyl-O-[1-alkyl-3,4-trimethylene-pyrazol(5)yl]-thionothiolphosphoric acid ester of the formula

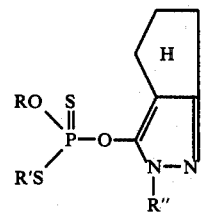

(I), in which
  R and R' each independently is alkyl with 1 to 6 carbon atoms, and
  R" is alkyl with 1 to 4 carbon atoms or cyanoalkyl with 1 to 4 carbon atoms in the alkyl radical, which possess arthropodicidal properties.

10 Claims, No Drawings

O,S-DIALKYL-O-[1-ALKYL-3,4-TRIMETHYLENE-PYRAZOL(5)YL]-THIONOTHIOLPHOSPHORIC ACID ESTER

The present invention relates to and has for its objects the provision of particular new O,S-dialkyl-O-[1-alkyl-3,4-trimethylene-pyrazol(5)yl]-thionothiolphosphoric acid esters which possess arthropodicidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from Netherlands Published Patent Application No. 7,209,051 and U.S. Pat. No. 2,754,244 that pyrazolothionophosphoric (phosphonic) acid esters, for example O,O-dimethyl- and O,O-diethyl-O-[1-methyl- or 1-phenyl-3-methyl-4-chloro-pyrazol(5)yl-]-and O,O-diethyl-O-[3-methyl- or -1-(2-cyano-ethyl)-3-methyl-4-chloro-pyrazol(5)yl]-thionophosphoric acid esters and O-ethyl-O-[1-phenyl-3-methyl-4-chloro-pyrazol(5)yl]-thionoethanephosphonic acid ester, possess insecticidal and acaricidal properties.

The present invention now provides, as new compounds, the O,S-dialkyl-O-pyrazolothionothiolphosphoric acid esters of the general formula

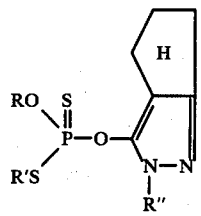

in which
R and R' each independently is alkyl with 1 to 6 carbon atoms, and
R" is alkyl with 1 to 4 carbon atoms or cyanoalkyl with 1 to 4 carbon atoms in the alkyl radical.

Preferably, R represents straight-chain or branched alkyl with 1 to 3 carbon atoms, especially ethyl, R' represents straight-chain or branched alkyl with 1 to 4 carbon atoms, especially n-propyl, and R" represents straight-chain or branched alkyl with 1 to 3 carbon atoms or cyanoalkyl with 1 to 3 carbon atoms in the alkyl radical.

Surprisingly, the D,S-dialkyl-O-pyrazolothionothiolphosphoric acid esters according to the invention possess a better insecticidal and acaricidal action than the compounds of analogous structure, and of the same type of action, previously known from the state of the art. The products of the present invention thus represent a genuine enrichment of the art.

The present invention also provides a process for the preparation of an O,S-dialkyl-O-pyrazolothionothiolphosphoric acid ester of the formula (I), in which a 5-hydroxypyrazole derivative of the general formula

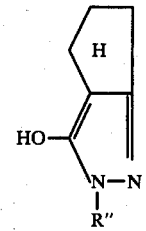

in which
R" has the abovementioned meaning,
is reacted, as such in the presence of an acid acceptor or in the form of an alkali metal salt, alkaline earth metal salt or ammonium salt thereof, with an O,S-dialkylthionothiolphosphoric acid diester halide of the general formula

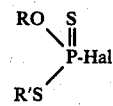

in which
R and R' have the aforementioned meanings and
Hal represents halogen, preferably chlorine, if appropriate in the presence of a solvent.

If, for example, O-ethyl-S-n-propyl-thionothiolphosphoric acid diester chloride and 1-(2-cyano-n-supply)-5-hydroxy-3,4-trimethylene-pyrazole are used as starting materials, the course of the reaction can be represented by the following equation:

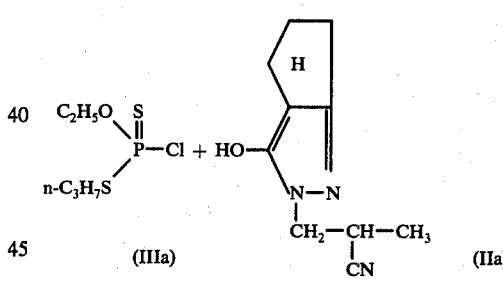

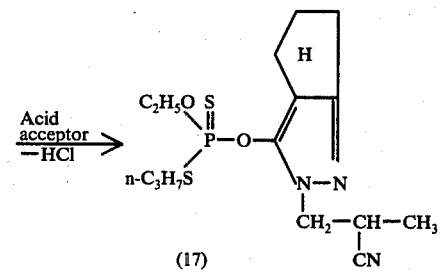

The 5-hydroxypyrazole derivatives (II) to be used as starting materials are disclosed in U.S. Pat. No. 3,768,065 and can be prepared in an analogous manner to the known compounds.

The following may be mentioned as individual examples of these compounds: 1-methyl-, 1-n-propyl-, 1-isopropyl-, 1-(2-cyano-n-propyl)-, 1-(2-cyanoethyl)- and 1-(1-cyanoethyl)-5-hydroxy-3,4-trimethylenepyrazole.

Furthermore, the O,S-dialkylthionothiolphosphoric acid diester halides (III) to be used as starting materials are known from the literature, e.g. U.S.S.R. Patent Specification No. 184,863.

The following may be mentioned as specific examples of these compounds: O,S-dimethyl-, O,S-diethyl-, O,S-di-n-propyl-, O,S-di-iso-propyl-, O-methyl-S-ethyl-, O-methyl-S-n-propyl-, O-methyl-S-iso-propyl-, O-methyl-S-n-butyl-, O-methyl-S-iso-butyl-, O-methyl-S-sec.-butyl-, O-ethyl-S-methyl-, O-ethyl-S-n-propyl-, O-ethyl-S-iso-propyl-, O-ethyl-S-n-butyl-, O-ethyl-iso-butyl-, O-ethyl-S-sec.-butyl-, O-n-propyl-S-methyl-, O-n-propyl-S-ethyl-, O-n-propyl-S-iso-propyl-, O-n-propyl-S-n-butyl-, O-n-propyl-S-sec.-butyl-, O-n-propyl-S-iso-butyl-, O-iso-propyl-S-methyl-, O-iso-propyl-S-ethyl-, D-iso-propyl-S-n-propyl-, O-iso-propyl-S-n-butyl- and O-iso-propyl-S-sec.-butyl-thionothiolphosphoric acid diester chloride.

The process for the preparation of the compounds according to the invention is preferably carried out in the presence of a suitable solvent or diluent. Practically all inert organic solvents can be used for this purpose, especially aliphatic and aromatic, optionally chlorinated hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at between 0° and 120° C, preferably at 50° to 80° C.

In general, the reaction is allowed to take place under normal pressure.

In carrying out the process, the starting components are in most cases employed in equimolar amounts. An excess of one or other reactant produces no significant advantages. The reaction is preferably carried out in one of the stated solvents, in the presence of an acid acceptor, at an elevated temperature. After the reaction has ended, the reaction mixture is cooled, poured into water and extracted by shaking with an organic solvent, for example methylene chloride. After phase separation, the organic phase is worked up in the usual manner by washing, drying and distilling off the solvent.

The new compounds are obtained in the form of oils, which in some cases cannot be distilled without decomposition, but are freed from the last volatile constituents by so-called "slight distillation", that is to say by prolonged heating under reduced pressure to moderately elevated temperatures, and are purified in this way. They are characterized by the refractive index.

As already mentioned, the O,S-dialkyl-O-pyrazolothionothiolphosphoric acid esters according to the invention are distinguished by an outstanding insecticidal and acaricidal activity. They are active against plant pests, pests harmful to health and pests of stored products. They possess a low phytotoxicity and a good action against both sucking and biting insects and against mites.

For this reason, the compounds according to the invention can be employed successfully as pesticides in plant protection as well as in the hygiene field and the field of protection of stored products.

The active compounds are well tolerated by plants, have a favorable level of toxicity to warm-blooded animals, and can be used for combating arthropod pests, especially insects and arachnidae which are encountered in agriculture, in forestry, in the protection of stored products and of materials, and in the hygiene field. They are active against normally sensitive and resistant species and against all or some stages of development. The abovementioned pests include:

From the class of the *Isopoda*, for example *Oniscus asellus, Armadillidium vulgare* and *Porcellio scaber;* from the class of the *Diplopoda*, for example *Blaniulus guttulatus;* from the class of the *Chilopoda*, for example *Geophilus carpophagus* and *Scutigera* spec.; from the class of the *Symphyla*, for example *Scutigerella immaculata;* from the order of the *Thysanura*, for example *Lepisma saccharina;* from the order of the *Collembola*, for example *Onychiurus armatus;* from the order of the *Orthoptera*, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the *Dermaptera*, for example *Forficula auricularia;* from the order of the *Isoptera*, for example *Reticulitermes* spp.; from the order of the *Anoplura*, for example *Phylloxera vastatrix, Pemphigus* spp., *Pediculus humanus corporis, Haematopinus* spp. and *Linognathus* spp.; from the order of the *Mallophaga*, for example *Trichodectes* spp. and *Damalinea spp.; from the order of the Thysanoptera*, for example *Hercinothrips femoralis* and *Thrips tabaci;* from the order of the *Heteroptera*, for example *Eurygaster* spp.; *Dysdercus intermedius, Piesma quadrata, Cimex lectularius, Rhodnius prolixus* and *Triatoma* spp.; from the order of the *Homoptera*, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, macrosiphum avanae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvanta lugens, Aonidiella aurantii, Aspidiotus hederae, Pseudococcus* spp. and *Psylla* spp.; from the order of the *Lepidoptera*, for example *Pectinophora gossypiella, Bupalus piniarius, Cheimatobia brumata, Lithocolletis blancardella, Hyponomeuta padella, Plutella maculipennis, Malacosoma neustria;, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Cacoecia podana, Capua reticulana, Chloristoneura fumiferana, Clysia ambiguella, Homona magnanima* and *Tortrix viridana;* from the order of the *Coleoptera*, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogo-*

*derma* spp., *Anthrenus* spp., *Atagenus* spp., *Lyctus* spp., *Meligethes aeneus, Ptinus* spp., *Niptus holoeucus, Gibbium psylloides, Tribolium* spp., *Tenebrio molitor, Agriotes* spp., *Conoderus* spp., *Melolontha melolontha, Amphimallon solstitialis* and *Costelyrtra zealandica;* from the order of the *Hymenoptera,* for example *Diprion* spp., *Hoplocampa* spp., *Lasius* spp., *Monomorium pharaonis* and *Vespa* spp.; from the order of the *Diptera,* for example *Aedes* spp., *Ancpheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa;* from the order of the *Siphonaptera,* for example *Xenopsylla cheopis* and *Ceratophyllus* spp.; from the class of the *Arachnida,* for example *Scorpio maurus* and *Latrodectus mactans;* from the order of the *Acarina,* for example *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp. and *Tetranychus* spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water, as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. suface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicide, or nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compound can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. arthropods such as insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention along or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Plutella test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% meant that all the caterpillars were killed, whereas 0% meant that none of the caterpillars were killed.

The active compounds, the concentrations of the active compounds, the evaluation times and the results can be seen from the following table:

Table 1

| (*Plutella* test) | | |
|---|---|---|
| Active compound | Active compound concentration in % | Degree of destruction in % after 3 days |
| (known) (A) | 0.1 | 100 |
| | 0.01 | 100 |
| | 0.001 | 0 |
| (known) (B) | 0.1 | 100 |
| | 0.01 | 100 |
| | 0.001 | 0 |
| (known) (C) | 0.1 | 100 |
| | 0.01 | 60 |
| | 0.001 | 0 |
| (known) (D) | 0.1 | 55 |
| | 0.01 | 0 |
| (known) (E) | 0.1 | 100 |
| | 0.01 | 50 |
| | 0.001 | 0 |
| (known) (F) | 0.1 | 100 |
| | 0.01 | 100 |
| | 0.001 | 0 |

Table 1-continued
(Plutella test)

| Active compound | Active compound concentration in % | Degree of destruction in % after 3 days |
|---|---|---|
| (known) (G): $C_2H_5$, $C_2H_5O$ — P(=S)—O—C(Cl)=C(CH_3)—... N—N—phenyl | 0.1 / 0.01 / 0.001 | 100 / 100 / 0 |
| (2): $C_2H_5O$, n-$C_3H_7S$ — P(=S)—O—[cyclopentylidene with H]—N—N—CH_3 | 0.1 / 0.01 / 0.001 | 100 / 100 / 100 |
| (5): $C_2H_5O$, n-$C_3H_7S$ — P(=S)—O—[cyclopentylidene with H]—N—N—$C_3H_7$-iso | 0.1 / 0.01 / 0.001 | 100 / 100 / 100 |
| (10): $C_2H_5O$, n-$C_3H_7S$ — P(=S)—O—[cyclopentylidene with H]—N—N—CH_2—CH_2—CN | 0.1 / 0.01 / 0.001 | 100 / 100 / 100 |
| (16): $C_2H_5O$, n-$C_3H_7S$ — P(=S)—O—[cyclopentylidene with H]—N—N—CH_2—CH(CN)—CH_3 | 0.1 / 0.01 / 0.001 | 100 / 100 / 100 |
| (3): $C_2H_5O$, n-$C_4H_9S$ — P(=S)—O—[cyclopentylidene with H]—N—N—CH_3 | 0.1 / 0.01 / 0.001 | 100 / 100 / 90 |
| (1): $C_2H_5O$, n-$C_4H_9S$ — P(=S)—O—[cyclopentylidene with H]—N—N—CH_2—CH(CN)—CH_3 | 0.1 / 0.01 / 0.001 | 100 / 100 / 100 |

EXAMPLE 2

Myzus test (contact action)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (Brassica oleracea) which had been heavily infested with peach aphids (Myzus persicae) were sprayed with the preparation of the active compound until dripping wet.

After the specified periods of time, the degree of destruction was determined as a percentage: 100% meant that all the aphids were killed, whereas 0% meant that none of the aphids were killed.

The active compounds, the concentrations of the active compounds, the evaluation times and the results can be seen from the following table:

Table 2
(Myzus test)

| Active compound | Active compound concentration in % | Degree of destruction in % after 1 day |
|---|---|---|
| (known) (B): $(CH_3O)_2$P(=S)—O—C(Cl)=C(CH_3)—...N—N—phenyl | 0.1 / 0.01 | 20 / 0 |
| (known) (F): $(C_2H_5O)_2$P(=S)—O—C(Cl)=C(CH_3)—...N—N—phenyl | 0.1 / 0.01 | 90 / 0 |

Table 2-continued
(*Myzus* test)

| Active compound | Active compound concentration in % | Degree of destruction in % after 1 day |
|---|---|---|
| (known) (G) [structure: C₂H₅−P(=S)(OC₂H₅)−O−C(=C(Cl)(C(CH₃)=N−N(C₆H₅)))] | 0.1<br>0.01 | 40<br>0 |
| (4) [structure: C₂H₅O−P(=S)(SCH₃)−O−C(=cyclopentylidene)−N(CH₃)−N] | 0.1<br>0.01 | 100<br>100 |
| (9) [structure: CH₃O−P(=S)(S−n-C₃H₇)−O−C(=cyclopentylidene)−N(C₃H₇-iso)−N] | 0.1<br>0.01 | 100<br>100 |
| (8) [structure: iso-C₃H₇O−P(=S)(S−n-C₃H₇)−O−C(=cyclopentylidene)−N(C₃H₇-iso)−N] | 0.1<br>0.01 | 100<br>99 |
| (7) [structure: n-C₃H₇O−P(=S)(S−n-C₃H₇)−O−C(=cyclopentylidene)−N(C₃H₇-iso)−N] | 0.1<br>0.01 | 100<br>99 |
| (12) [structure: n-C₃H₇O−P(=S)(S−n-C₃H₇)−O−C(=cyclopentylidene)−N(CH₂−CH₂−CN)−N] | 0.1<br>0.01 | 100<br>98 |
| (11) [structure: C₂H₅O−P(=S)(S−n-C₄H₉)−O−C(=cyclopentylidene)−N(CH₂−CH₂−CN)−N] | 0.1<br>0.01 | 100<br>85 |

EXAMPLE 3

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all the spider mites were killed, whereas 0% meant that none of the spider mites were killed.

The active compounds, the concentrations of the active compounds, the evaluation times and the results can be seen from the following table:

Table 3
(*Tetranychus* test/resistant)

| Active compound | Active compound concentration in % | Degree of destruction in % after 2 days |
|---|---|---|
| (known) (A) [structure: (CH₃O)₂P(=S)−O−C(=C(Cl)(C(CH₃)=N−N(CH₃)))] | 0.1 | 0 |
| (known) (B) [structure: (CH₃O)₂P(=S)−O−C(=C(Cl)(C(CH₃)=N−N(C₆H₅)))] | 0.1 | 0 |

Table 3-continued
(Tetranychus test/resistant)

| Active compound | Active compound concentration in % | Degree of destruction in % after 2 days |
|---|---|---|
| (C₂H₅O)₂P(S)—O—C(Cl)=C(CH₃)—N=N—N(CH₃) (known) (D) | 0.1 | 0 |
| (C₂H₅O)₂P(S)—O—C(Cl)=C(CH₃)—N=N—N(CH₂—CH₂—CN) (known) (E) | 0.1 | 0 |
| (C₂H₅O)₂P(S)—O—C(Cl)=C(CH₃)—N=N—N(C₆H₅) (known) (F) | 0.1 | 0 |
| (C₂H₅)(C₂H₅O)P(S)—O—C(Cl)=C(CH₃)—N=N—N(C₆H₅) (known) (G) | 0.1 | 0 |
| C₂H₅O, n-C₃H₇S—P(S)—O—[cyclopentane-fused pyrazole, N-CH₃] (2) | 0.1 | 98 |
| CH₃O, n-C₃H₇S—P(S)—O—[cyclopentane-fused pyrazole, N-C₃H₇-iso] (9) | 0.1 | 100 |
| C₂H₅O, n-C₃H₇S—P(S)—O—[cyclopentane-fused pyrazole, N-C₃H₇-iso] | 0.1 | 100 |

Table 3-continued
(Tetranychus test/resistant)

| Active compound | Active compound concentration in % | Degree of destruction in % after 2 days |
|---|---|---|
| (5) C₂H₅O, n-C₃H₇S—P(S)—O—[cyclopentane-fused pyrazole, N-CH₂—CH(CN)—CH₃] | 0.1 | 100 |
| (16) C₂H₅O, n-C₄H₉S—P(S)—O—[cyclopentane-fused pyrazole, N-CH₃] (3) | 0.1 | 99 |

The process of the invention is illustrated by the following preparative examples.

EXAMPLE 4

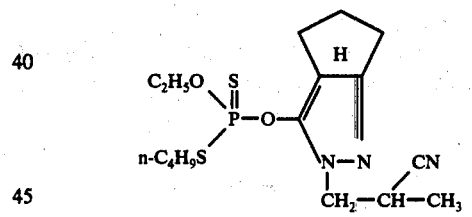

(1)

23g (0.1 mole) of O-ethyl-S-n-butyl-thionothiolphosphoric acid diester chloride were poured into a suspension of 19 g (0.1 mole) of 1-(2icyano-propyl)-5-hydroxy-3,4-trimethylenepyrazole and 15 g of potassium carbonate in 200 ml of acetonitrile. The reaction mixture was heated to 60°–65° C for 3 hours, cooled, poured into 500 ml of water and taken up in 500 ml of methylene chloride; the organic phase was separated off. It was additionally washed 3 times with 300 ml of water at a time, and dried over sulfate and the solvent was evaporated off. The residue was subjected to slight distillation. 31 g (80% of theory) of O-ethyl-S-n-butyl-O-[1-(2-cyano-n-propyl)-3,4-trimethylene-pyrazol(5)yl]-thionothiolphosphoric acid ester having a refractive index $n_D^{20}$ of 1.5375 were obtained.

The following compounds of the formula

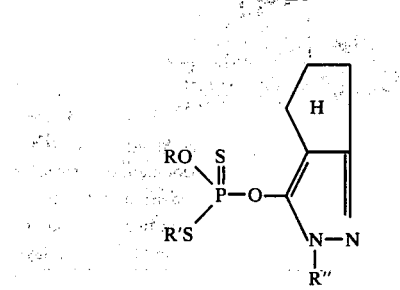

(I)

could be prepared analogously:

Table 4

| Compound No. | R | R' | R" | Refractive index |
|---|---|---|---|---|
| 2 | $C_2H_5-$ | $n\text{-}C_3H_7-$ | $-CH_3$ | $n_D^{20}:1.5448$ |
| 3 | $C_2H_5-$ | $n\text{-}C_4H_9-$ | $-CH_3$ | $n_D^{24}:1.5410$ |
| 4 | $C_2H_5-$ | $CH_3-$ | $-CH_3$ | $n_D^{23}:1.5600$ |
| 5 | $C_2H_5-$ | $n\text{-}C_3H_7-$ | $-C_3H_7\text{-iso}$ | $n_D^{25}:1.5330$ |
| 6 | $\text{iso-}C_3H_7-$ | $n\text{-}C_4H_9-$ | $-C_3H_7\text{-iso}$ | $n_D^{25}:1.5259$ |
| 7 | $n\text{-}C_3H_7-$ | $n\text{-}C_3H_7-$ | $-C_3H_7\text{-iso}$ | $n_D^{25}:1.5310$ |
| 8 | $\text{iso-}C_3H_7-$ | $n\text{-}C_3H_7-$ | $-C_3H_7\text{-iso}$ | $n_D^{25}:1.5309$ |
| 9 | $CH_3-$ | $n\text{-}C_3H_7-$ | $-C_3H_7\text{-iso}$ | $n_D^{25}:1.5442$ |
| 10 | $C_2H_5-$ | $n\text{-}C_3H_7-$ | $-CH_2-CH_2-CN$ | $n_D^{23}:1.5459$ |
| 11 | $C_2H_5-$ | $n\text{-}C_4H_9-$ | $-CH_2-CH_2-CN$ | $n_D^{23}:1.5420$ |
| 12 | $n\text{-}C_3H_7-$ | $n\text{-}C_3H_7-$ | $-CH_2-CH_2-CN$ | $n_D^{22}:1.5418$ |
| 13 | $C_2H_5-$ | $CH_3$ | $-CH_2-CH_2-CN$ | $n_D^{20}:1.5592$ |
| 14 | $\text{iso-}C_3H_7-$ | $n\text{-}C_4H_9-$ | $-CH_2-CH_2-CN$ | $n_D^{20}:1.5424$ |
| 15 | $\text{iso-}C_3H_7-$ | $n\text{-}C_3H_7-$ | $-CH_2-CH_2-CN$ | $n_D^{20}:1.5372$ |
| 16 | $C_2H_5-$ | $n\text{-}C_3H_7-$ | $-CH_2-CH-CH_3$ $\quad\quad\quad\;\; \vert$ $\quad\quad\quad\;\; CN$ | $n_D^{20}:1.5392$ |

It will be appreciated that the instant specification and examples are set forth by way of illustration and not limitation, and that various modifications and changes may be made without departing from the spirit and scope of the present invention.

What is claimed is:

1. An O,S-dialkyl-O-[1-alkyl-3,4-trimethylene-pyrazol(5)yl]-thionothiolphosphoric acid ester of the formula

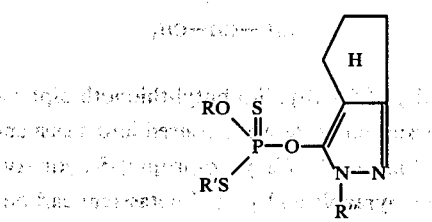

in which
R and R' each independently is alkyl with 1 to 6 carbon atoms, and
R" is alkyl with 1 to 4 carbon atoms or cyanoalkyl with 1 to 4 carbon atoms in the alkyl radical.

2. An ester according to claim 1, in which R is alkyl with 1 to 3 carbon atoms, R' is alkyl with 1 to 4 carbon atoms, and R" is alkyl with 1 to 3 alkyl atoms or cyanoalkyl with 1 to 3 carbon atoms in the alkyl radical.

3. The compound according to claim 1 wherein such compound is O-ethyl-S-n-propyl-O-[1-methyl-3,4-trimethylene-pyrazol(5)yl]-thionothiolphosphoric acid ester of the formula 4. The compound according to claim 1 wherein such compound is O-ethyl-S-n-butyl-O-[1-methyl-3,4-trimethylene-pyrazol(5)yl]-thionothiolphosphoric acid ester of the formula

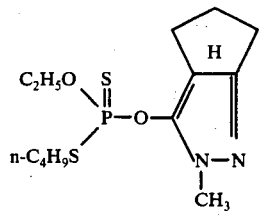

5. The compound according to claim 1 wherein such compound is O-ethyl-S-n-propyl-O-[1-isopropyl-3,4-trimethylene-pyrazol(5)yl]-thionothiolphosphoric acid ester of the formula

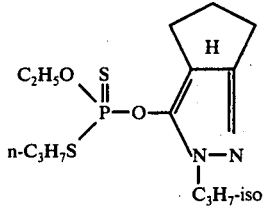

6. The compound according to claim 1 wherein such compound is O-ethyl-S-n-propyl-O-[1-(2-cyanoethyl)-3,4-trimethylene-pyrazol(5)yl]-thionothiolphosphoric acid ester of the formula

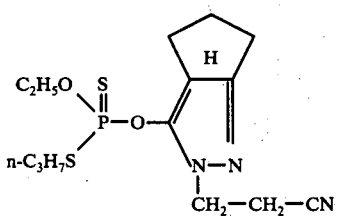

7. The compound according to claim 1 wherein such compound is O-ethyl-S-n-propyl-O-[1-(2-cyano-n-propyl)-3,4-trimethylene-pyrazol(5)yl]-thionothiolphosphoric acid ester of the formula

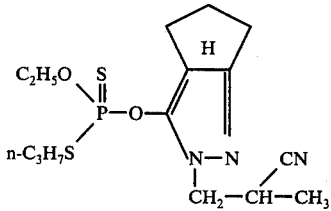

8. An arthropodicidal composition containing as active ingredient an arthropodicidally effective amount of an ester according to claim 1 in admixture with a diluent.

9. A method of combating arthropods which comprises applying to the arthropods or to a habitat thereof, an arthropodicidally effective amount of an ester according to claim 1.

10. The method according to claim 9 in which said compound is
O-ethyl-S-n-propyl-O-[1-methyl-3,4-trimethylene-pyrazol(5)yl]-thionothiolphosphoric acid ester,
O-ethyl-S-n-butyl-O-[1-methyl-3,4-trimethylene-pyrazol(5)yl]-thionothiolphosphoric acid ester,
O-ethyl-S-n-propyl-O-[1-isopropyl-3,4-trimethylene-pyrazol-(5)yl]-thionothiolphosphoric acid ester,
O-ethyl-S-n-propyl-O-[1-(2-cyanoethyl)-3,4-trimethylene-pyrazol(5)yl]-thionothiolphosphoric acid ester, or
O-ethyl-S-n-propyl-O-[1-(2-cyano-n-propyl)-3,4-trimethylene-pyrazol(5)yl]-thionothiolphosphoric acid ester.

* * * * *

UNITED STATES PATENT AND TRADEMARK OFFICE
CERTIFICATE OF CORRECTION

PATENT NO. : 4,075,330            Page 1 of 2
DATED : February 21, 1978
INVENTOR(S) : Hellmut Hoffmann and Ingeborg Hammann It is certified that error appears in the above-identified patent and that said Letters Patent are hereby corrected as shown below:

| | |
|---|---|
| Title page, priority | change "Feb. 26" to -- Feb. 25 --. |
| Col. 1, line 57 | change "D," to -- O, --. |
| Col. 2, line 27 | change "aforementioned" to -- abovementioned -- |
| Col. 2, line 31 | change "-supply)" to -- -propyl) --. |
| Col. 2, line 61 | change "3,768,065" to -- 3,786,065 --. |
| Col. 3, line 14 | change "D-iso-" to -- O-iso- --. |
| Col. 4, line 39 | change "tabacl" to -- tabaci --. |
| Col. 4, line 42 | change "macrosiphum" to -- Macrosiphum --. |
| Col. 4, line 46 | change "Nilaparvanta" to -- Nilaparvata --. |
| Col. 4, lines 58-59 | change "Chloristoneura" to -- Choristoneura -- |
| Col. 5, line 1 | change "Atagenus" to -- Attagenus --. |
| Col. 5, line 5 | change "Costelyrtra" to -- Costelytra --. |
| Col. 5, line 9 | change "Aedes" to -- Aëdes --. |
| Col. 6, line 43 | change "arthropodicide" to -- arthropodicides -- |
| Col. 7, line 4 | change "compound" to -- compounds --. |

UNITED STATES PATENT AND TRADEMARK OFFICE
CERTIFICATE OF CORRECTION

PATENT NO. : 4,075,330
DATED : February 21, 1978
INVENTOR(S) : Hellmut Hoffmann and Ingeborg Hammann It is certified that error appears in the above-identified patent and that said Letters Patent are hereby corrected as shown below:

Col. 7, line 31    change "along" to -- alone --.

Col. 10, line 49   change "0,01" to -- 0.01 --.

Col. 14, line 50   change "(2icyano-" to -- (2-cyano-n --.

Signed and Sealed this

Twenty-fifth Day of July 1978

[SEAL]

Attest:

RUTH C. MASON
Attesting Officer

DONALD W. BANNER
Commissioner of Patents and Trademarks